United States Patent [19]
François et al.

[11] Patent Number: 6,077,843
[45] Date of Patent: Jun. 20, 2000

[54] AQUEOUS SUSPENSIONS OF 9-HYDROXYRISPERIDONE FATTY ACID ESTERS

[75] Inventors: Marc Karel Jozef François, Kalmthout; Roger Carolus Augusta Embrechts, Oud-Turnhout; Herman Karel Borghijs, Willebroek; Johan Monbaliu, Turnhout, all of Belgium

[73] Assignee: Janssen Pharmaceutica, N.V., Beerse, Belgium

[21] Appl. No.: 09/180,659

[22] PCT Filed: May 12, 1997

[86] PCT No.: PCT/EP97/02504

§ 371 Date: Nov. 12, 1998

§ 102(e) Date: Nov. 12, 1998

[87] PCT Pub. No.: WO97/44039

PCT Pub. Date: Nov. 27, 1997

[30] Foreign Application Priority Data

May 20, 1996 [EP] European Pat. Off. ............ 96 201 429

[51] Int. Cl.[7] .................................................. A61K 31/505
[52] U.S. Cl. .............................................................. 514/258
[58] Field of Search .............................................. 514/258

[56] References Cited

U.S. PATENT DOCUMENTS

| | | | |
|---|---|---|---|
| 5,158,952 | 10/1992 | Janssen et al. | 514/258 |
| 5,254,556 | 10/1993 | Janssen et al. | 514/258 |
| 5,612,346 | 3/1997 | Mesens et al. | 514/258 |
| 5,650,173 | 7/1997 | Ramstack et al. | 424/489 |
| 5,654,008 | 8/1997 | Herbert et al. | 424/489 |
| 5,688,801 | 11/1997 | Mesens et al. | 514/258 |
| 5,770,231 | 6/1998 | Mesens et al. | 424/497 |
| 5,792,477 | 8/1998 | Rickey et al. | 424/501 |
| 5,916,598 | 6/1999 | Rickey et al. | 424/501 |

FOREIGN PATENT DOCUMENTS 0 368 388  5/1990  European Pat. Off..
WO 96 39397  12/1996  WIPO.

*Primary Examiner*—Keith D. MacMillan
*Attorney, Agent, or Firm*—Mary Appollina

[57] ABSTRACT

The present invention is concerned with a pharmaceutical composition suitable as a depot formulation for administration via intramuscular or subcutaneous injection, comprising:

(1) as an active ingredient a therapeutically effective amount of a 9-hydroxyrisperidone fatty acid ester or a salt, or a stereoisomer or a stereoisomeric mixture thereof and (2) a pharmaceutically acceptable carrier;

wherein the pharmaceutically acceptable carrier is water and the active ingredient is suspended therein; and with a process of preparing such a composition. The invention further concerns such a pharmaceutical composition for use as a medicament in the treatment of schizophrenia, non-schizophrenic psychoses, behavioural disturbances associated with neurodegenerative disorders, e.g. in dementia, behavioural disturbances in mental retardation and autism, bipolar mania, depression, anxiety.

10 Claims, No Drawings

AQUEOUS SUSPENSIONS OF 9-HYDROXYRISPERIDONE FATTY ACID ESTERS

CROSS REFERENCE TO RELATED APPLICATIONS

This application is a National Stage application under 35 U.S.C. § 371 of PCT/EP97/02504 filed May 12, 1997, which claims priority from EP 96.201.429.6, filed May 20, 1996.

The present invention is concerned with a pharmaceutical composition suitable as a depot formulation for administration via intramuscular or subcutaneous injection, comprising:

(1) as an active ingredient a therapeutically effective amount of a 9-hydroxyrisperidone fatty acid ester or a salt, or a stereoisomer or a stereoisomeric mixture thereof and (2) a pharmaceutically acceptable carrier; wherein the pharmaceutically acceptable carrier is water and the active ingredient is suspended therein;

and with a process of preparing such a composition. The invention further involves such a pharmaceutical composition for use as a medicament in the treatment of schizophrenia, non-schizophrenic psychoses, behavioural disturbances associated with neurodegenerative disorders, e.g. in dementia, behavioural disturbances in mental retardation and autism, bipolar mania, depression, anxiety.

Risperidone is generic to 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one. The preparation and pharmacological activity thereof are described in EP-0,196,132 (corresponding to U.S. Pat. No. 4,804,663). Various conventional pharmaceutical dosage forms, including tablets, capsules, drops, suppositories, oral solutions and injectable solutions are exemplified therein. In practice, risperidone is normally administered as the base in a tablet or in a buffered, oral or intramuscular solution. Particular solutions for oral or intramuscular administration are described in WO-96/01652.

Risperidone is a highly potent drug having a relatively narrow therapeutic index. It may produce undesirable side effects on overdosage, most notably extra pyramidal syndrome (EPS) and to a lesser extent hypotension (due to peripheral alpha-adrenergic activity). For the purpose of producing an antipsychotic effect in a patient the total daily dose of risperidone ranges from about 2 to about 8 mg; for the alleviation of behavioral disturbances associated with neurodegenerative disorders the total daily dose is usually less and typically ranges from about 0.5 to about 2 mg. Inter-individual differences and co-medication may necessitate dose titrating in patients.

For a number of reasons, it is desirable to administer risperidone in a sustained or delayed release (depot) formulation which is effective over an extended period of time, preferably about 3 weeks or more.

WO-94/25460 (corresponding to EP-0,697,019) relates to a first such depot formulation and concerns the risperidone pamoate salt, a poorly water-soluble salt form of risperidone, which may be suspended in a pharmaceutically acceptable carrier, such as water or an oil, and may be administered subcutaneously or intramuscularly. This salt, however, has pharmacokinetic properties which are suboptimal. The release of the active ingredient from the formulations appears to be too rapid, which results in relatively high initial plasma levels and an inadequate mean duration of action, both characteristics which should be improved upon in a truly effective depot formulation.

WO-95/13814 concerns sustained release formulations for parenteral administration wherein risperidone is microencapsulated in a biocompatible, biodegradable wall-forming material (e.g. a polymer such as dl-(polylactide-co-glycolide)). The micro-encapsulated formulations have suitable pharmacokinetic properties, but require sophisticated processes of preparation in a purpose-built plant.

Consequently, there is still a need for an effective and readily available depot formulation of risperidone or a risperidone-like compound.

It is known that risperidone is metabolized to 9-hydroxyrisperidone which has a pharmacological profile and potency comparable with that of the parent drug risperidone, but which has a longer elimination half-life. Risperidone is distributed to and eliminated from the brain tissues more rapidly than its metabolite 9-hydroxyrisperidone. 9-hydroxyrisperidone, its enantiomeric forms and the $C_{2-20}$ alkanoic acid esters thereof are described in EP-0,368,388 (corresponding to U.S. Pat No. 5,158,952 and U.S. Pat. No. 5,254,556). Said esters are considered to be potentially valuable prodrugs of the active metabolite of risperidone for use in depot formulations.

In addition, the problems associated with the genetic polymorphism in the metabolism of risperidone to its active metabolite 9-hydroxyrisperidone can possibly be avoided by administration of the metabolite or a long-acting prodrug thereof, instead of risperidone itself.

Indeed, in the metabolism of risperidone, debrisoquine-type genetic polymorphism plays a distinct role. As a consequence, humans can be phenotyped as poor, intermediate or extensive metabolizers on the basis of their metabolic ratio. Said metabolic ratio is defined as the ratio of urine recovery of debrisoquine to that of the 4-hydroxymetabolite of debrisoquine over a period of 8 hours after an oral intake of 10 mg debrisoquine. In oriental people more than 99% of the population can be phenotyped as extensive metabolizers and poor metabolizers are rather seldom. In the Caucasian race however only about 90% of the population can be phenotyped as either extensive or intermediate metabolizers. Approximately 10% of the population are poor metabolizers and have deficient amounts of the debrisoquine-hydroxylase enzyme.

The duration of action and the peak plasma levels of active agents (risperidone and 9-hydroxyrisperidone) are dependent on the debrisoquine metabolic ratio of the human subject treated with risperidone. More in particular, in poor metabolizers high transient peak levels of risperidone are likely to be attained when the total daily amount is administered in a single dose. This may give rise to undesired side-effects such as extra pyramidal syndrome (EPS) and hypotension.

Further inter-individual differences among humans, as far as the metabolism of risperidone is concerned, are due to the fact that in clinical practice the human subjects to be treated with risperidone will usually receive additional medication, e.g. tranquillizers such as phenothiazines, neuroleptica such as haloperidol, antidepressiva etc., all of which may compete with risperidone for the debrisoquine-hydroxylase enzyme. These drug interactions may seriously affect the metabolism of risperidone, especially in extensive metabolizers, and may result in the occurrence of adverse effects in patients receiving such additional medication.

The present invention results from the investigations into the development of an efficient, well-tolerated, sustained or delayed release (depot) formulation of a 9-hydroxyrisperidone alkanoic acid ester which is therapeutically effective for at least three weeks or more. By the expression "effective for at least three weeks or more", one means that the plasma levels of the active ingredient, 9-hydroxyrisperidone (free alcohol liberated by hydrolysis from the alkanoic acid ester), should be above approximately 10 ng/ml. On the other hand, said plasma levels should remain at all times below a threshold value of approximately 100 ng/ml in order for one to call the formulation "efficient". The threshold value is the mean plasma level during a considerable period of time, e.g. for more than 15 minutes, above which patients may experience undesirable side effects, or conversely, the value of the plasma level under which the systemic tolerance of the formulation in question is still acceptable. The threshold value does not hold for transient, high plasma levels during a short period of time, e.g. for less than 15 minutes, which are due, for example to unexpected burst-release of the active ingredient.

Both of the foregoing features—plasma levels above a minimal therapeutical concentration but below a side-effect producing threshold value—are considered to be basic requirements that a contemporary depot formulation should fulfil in order to be acceptable for the intended patients. Limiting the number of drug administrations and the occurrence of undesirable side effects after each administration will undoubtedly improve the patients' compliance with the therapy. However, beyond these basic requirements, a number of further desiderata can be identified which would further improve patients' compliance; the two most notable being good local tolerance and ease of administration.

Good local tolerance means minimal irritation and inflammation at the site of injection; ease of administration refers to the size of needle and length of time required to administer a dose of a particular drug formulation. In addition, depot formulations should be stable and have a shelf-life of at least two years under normal conditions.

The investigations into the development of an efficient, well-tolerated, sustained or delayed release (depot) formulation of a 9-hydroxyrisperidone alkanoic acid ester which fulfils the above mentioned requirements, led to the finding that a pharmaceutical composition suitable as a depot formulation for administration by intramuscular or subcutaneous injection should comprise:

(1) as an active ingredient a therapeutically effective amount of a 9-hydroxy-risperidone fatty acid ester having the formula

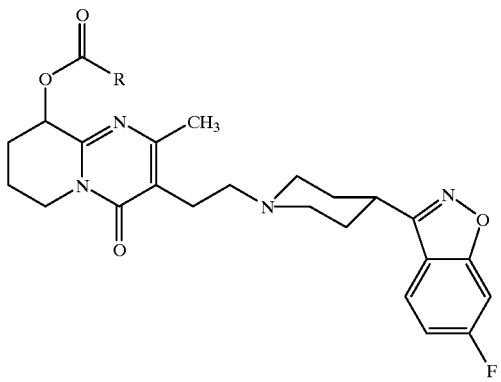

or a salt, or a stereoisomer or a stereoisomeric mixture thereof, wherein R represents a straight $C_{9-19}$alkyl radical; and (2) a pharmaceutically acceptable carrier;
characterized in that the pharmaceutically acceptable carrier is water and the active ingredient is suspended therein.

Surprisingly, it appears that aqueous suspensions of 9-hydroxyrisperidone $C_{10-20}$ alkanoic acid esters (wherein R represents a straight $C_{9-19}$ alkyl radical) are comparable and in some respects far better depot formulations than corresponding suspensions in non-aqueous, oily suspensions. This is quite unexpected since it is somewhat of a tenet in the art that depot formulations must comprise lipophilic drugs dissolved or suspended in a lipophilic medium. Hitherto, the 9-hydroxyrisperidone $C_{10-20}$ alkanoic acid esters were therefore formulated in oils suitable for intramuscular administration, in particular in sesame oil. $C_{10-20}$alkanoic acids are selected from the group consisting of decanoic (capric), undecanoic, dodecanoic (lauric), tridecanoic, tetradecanoic (myristic), pentadecanoic, hexadecanoic (palmitic), heptadecanoic, octadecanoic (stearic), nonadecanoic and eicosanoic acid. Due to their limited aqueous solubility, it was generally believed that the esters had to be suspended into oils. The ester having a $C_{15}$ (pentadecyl) chain and the active ingredient corresponding thereto being the 9-hydroxyrisperidone palmitate ester was found to be the superior ester from a pharmacokinetic, as well as from a tolerance point of view.

In order to improve the tolerance further, several suspensions with different size particles of 9-hydroxyrisperidone palmitate ester in sesame oil, optionally in the presence of aluminum monostearate, were next considered. No significant difference between small or large prodrug particles could be established. The presence of the aluminum monostearate only affected the viscosity of the formulation and its ease of administration. In yet another set of experiments, it was found that upon decreasing the prodrug concentration in the depot formulation, the tolerance to the administered formulation improved still further. Because the oil suspensions proved difficult to take up in a syringe, experiments with less viscous carriers were initiated, in particular with a medium-chain triglyceride (Miglyol™), and contrary to what the tenet holds, with water as a carrier. The Miglyol™ formulations exhibited considerably less systemic and local tolerance than the sesame oil based formulations. To our big surprise, however, the aqueous suspensions of the 9-hydroxyrisperidone palmitate ester outperformed the sesame oil based formulations. They have not only an appropriate duration of action, but also acceptable systemic and local tolerance, and a strikingly limited inter-individual variability of pharmacokinetic properties.

The pharmacokinetic properties of the aqueous suspensions according to the present invention further may depend to a limited extent on the physico-chemical properties of the 9-hydroxyrisperidone palmitate ester solid, such as the particle size and crystal form.

Aqueous compositions according to the present invention conveniently further comprise a suspending agent and a wetting agent, and optionally one or more of a preservative, a buffer and an isotonizing agent. Particular ingredients may function as two or more of these agents simultaneously. e.g. behave like a preservative and a buffer, or behave like a buffer and an isotonizing agent.

Suitable suspending agents for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxypropylene ethers. Preferably sodium carboxymethyl cellulose is used in a concentration of 0.5 to 2%, most preferably 1% (w/v). Suitable wetting agents for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of 0.05 to 0.3%, more preferably 0.05 to 0.2%, most preferably 0.1% (w/v).

Preservatives are antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-γ-piccolinium chloride, phenylmercuric acetate and thimerosal. In particular, it is benzyl alcohol which can be used in a concentration up to 2% (w/v), preferably up to 1.5% (w/v). Isotonizing agents are, for example, sodium chloride, dextrose, mannitol, sorbitol, lactose, sodium sulfate. The suspensions conveniently comprise from 1 to 10% (w/v) isotonizing agent. Preferably, mannitol is used in a concentration from 2 to 7%, more preferably about 5%. Most preferably, however, from about 1 to about 3% (w/v), especially from about 1.5 to about 2% (w/v) of one or more electrolytes are used to render the suspension isotonic, apparently because ions help to prevent flocculation of the suspended ester. In addition, particular electrolytes have the further advantage of buffering the aqueous suspension. Particularly preferred is the use of a mixture of disodium hydrogen phosphate (anhydrous) (typically about 0.9% (w/v)) and sodium dihydrogen phosphate monohydrate (typically about 0.6% (w/v)) for rendering the solution isotonic, neutral and less prone to flocculation of the suspended ester therein.

A particularly desirable feature for an injectable depot formulation relates to the ease with which it can be administered. In particular such an injection should be feasible using a needle as fine as possible in a span of time which is as short as possible. This can be accomplished with the aqueous suspensions of the present invention by keeping the viscosity below about 75 mPa.s, preferably below 60 mPa.s. Aqueous suspensions of such viscosity or lower can both easily be taken up in a syringe (e.g. from a vial), and injected through a fine needle (e.g a 21 G 1½, 22 G 2 or 22 G 1¼ needle).

Ideally, aqueous suspensions according to the present invention will comprise as much prodrug as can be tolerated so as to keep the injected volume to a minimum, and as little of the other ingredients as possible. In particular, such a composition will comprise by weight based on the total volume of the composition:

(a) from 3 to 20% (w/v) of the prodrug;

(b) from 0.05 to 0.2% (w/v) of a wetting agent;

(c) from 0.5 to 2% (w/v) of a suspending agent;

(d) up to 2% (w/v) preservatives;

(e) optionally one or more isotonizing agents sufficient to render the composition isotonic with serum; and (f) water q.s. ad 100%.

The aqueous suspensions according to the present invention can be prepared following art-known processes of preparing suspensions characterized by intimately mixing the active ingredient with the carrier.

Such a process may comprise the steps of:

(a) stirring the wetting agent with the water;

(b) adding the preservative to the mixture while stirring;

(c) dispersing the suspending agent in the mixture while stirring;

(d) optionally dissolving the isotonizing agent in the mixture while stirring;

(e) dispersing the active ingredient in the mixture while stirring, followed by homogenizing the mixture.

In view of the usefulness of 9-hydroxyrisperidone in the treatment of a number of disorders, the present invention also concerns a pharmaceutical composition as described hereinbefore for use as a medicament in the treatment of schizophrenia, non-schizophrenic psychoses, behavioural disturbances associated with neurodegenerative disorders, e.g. in dementia, behavioural disturbances in mental retardation and autism, bipolar mania, depression, anxiety.

In addition, the present invention concerns the use of a composition as described hereinbefore for the preparation of a medicament for treating schizophrenia, non-schizophrenic psychoses, behavioural disturbances associated with neurodegenerative disorders, e.g. in dementia, behavioural disturbances in mental retardation and autism, bipolar mania, depression, anxiety.

The present invention further concerns a method of treating warm-blooded animals, in particular humans suffering from schizophrenia, non-schizophrenic psychoses, behavioural disturbances associated with neurodegenerative disorders, e.g. in dementia, behavioural disturbances in mental retardation and autism, bipolar mania, depression, anxiety, said method comprising the administration of a therapeutically effective amount of an aqueous suspension as described hereinbefore. Typically, said formulation will be administered approximately every three weeks or even at longer intervals where possible. The dosage should range from about 2 to 4 mg/kg body weight.

The following examples are intended to illustrate the present invention.

Experimental Part

A. Preparation of 9-hydroxyrisperidone palmitate ester.

N,N'-Dicyclohexylcarbodiimide (1.39 g; 6.8 mmol) was added to a solution of hexadecanoic acid (1.54 g; 6 mmol) in dichloromethane (140 ml) and stirred at room temperature for 10 minutes. 9-hydroxyrisperidone (2.13 g; 5 mmol) was added to the reaction mixture, followed by 4pyrrolidinopyridine (93 mg; 0.63 mmol). The mixture was stirred for three days at room temperature. Water (200 ml) was added to the reaction mixture and this was extracted three times with chloroform (100 ml). The combined organic layers were dried (MgSO$_4$), filtered, and evaporated. The mixture was triturated in diisopropylether (100 ml), filtered and recrystalized in isopropanol (60 ml). The crystals were filtered off and dried, yielding 9-hydroxyrisperidone palmitate ester (2.67 g; 80.4%).

B. Composition Examples

Each of the formulations hereunder was prepared according to the following general recipe:

The wetting agent was stirred with the water at room temperature and the preservative was added thereto. While stirring, the suspending agent was dispersed in the mixture, and the isotonizing agent—if any—was added. Next, the active ingredient was dispersed into the stirred mixture which was then homogenized and filled into sterile containers. All ingredients and apparatus used during the preparation of the aqueous suspensions were sterile. In the tables hereunder, all concentrations are expressed as % weight by volume of the total formulation [% (w/v)].

Formulation 1 (F1)

| | |
|---|---|
| 9-hydroxyrisperidone palmitate* | 15.6% (10% 9-hydroxyrisperidone) |
| polysorbate 20 | 0.2% |
| sodium carboxymethyl cellulose 30 mPa · s | 2% |
| benzyl alcohol | 1.5% |
| water q.s. ad | 100% |

*The ester was milled, but not sieved.
Physico-chemical properties of F1
pH = 6.52
viscosity = 20 mPa · s
osmolality = ±210 mOsm/kg
Formulation 2a, 2b and 2c (F2a, F2b, F2c)

| | |
|---|---|
| 9-hydroxyrisperidone palmitate # | 7.8% (5% 9-hydroxyrisperidone) |
| polysorbate 20 | 0.1% |
| sodium carboxymethyl cellulose 30 mPa · s | 2% |
| benzyl alcohol | 1.5% |
| mannitol | 2% |
| water q.s. ad | 100% |

The ester was milled and sieved into three fractions:

| | |
|---|---|
| F2a (particle size <10 µm) | viscosity = 19 mPa · s |
| F2b (<10 µm < particle size < 30 µm) | viscosity = 29 mPa · s |
| F2c (particle size >20 µm) | viscosity = 32 mPa · s | pH = 6.86
osmolality = ±280 mOsm/kg
Formulation 3a, 3b and 3c (F3a, F3b, F3c)

| | |
|---|---|
| 9-hydroxyrisperidone palmitate # | 15.6% (10% 9-hydroxyrisperidone) |
| polysorbate 20 | 0.2% |
| sodium carboxymethyl cellulose 30 mPa · s | 1% |
| benzyl alcohol | 1.5% |
| mannitol | 2% |
| water q.s. ad | 100% |

The ester was milled and sieved into three fractions:

| | |
|---|---|
| F3a (particle size < 10 µm) | viscosity = 60 mPa · s |
| F3b (10 µm < particle size < 30 µm) | viscosity = 60 mPa · s |
| F3c (particle size > 30 µm) | viscosity = 60 mPa · s | pH = 6.74
osmolality = ±280 mOsm/kg
Formulation 4 (F4)

| | |
|---|---|
| 9-hydroxyrisperidone palmitate # | 7.8% (5% 9-hydroxyrisperidone) |
| polysorbate 20 | 0.2% |
| sodium carboxymethyl cellulose 30 mPa · s | 1% |
| benzyl alcohol parenteral | 1.5% |
| disodium hydrogen phosphate anhydrous | 0.9% |
| sodium dihydrogen phosphate monohydrate | 0.6% |
| water q.s. ad | 100% |

The ester was milled and sieved using appropriate nominal standard test sieves, yielding active ingredient having a particle size distribution as follows:

90% of the particles (by volume)≧0.5 µm

50% of the particles (by volume)≧5 µm

10% of the particles (by volume)≧15 µm.

The ester was sterilized by irradiation with 25 kGy $^{90}$Y and mixed with the solvent (filtered through a 0.22 µm membrane filter and autoclaved during 30 minutes at 121° C.) under sterile conditions.

pH=7 viscosity=±10 mPa.s osmolality=±450 mOsm/kg

The syringeability through a 22 G 1¼ needle posed no problem.

Formula 5a, 5b and 5c (F5a, F5b, F5c)

| | F5a | F5b | F5c |
|---|---|---|---|
| 9-hydroxyrisperidone palmitate # | 15.6% | 23.4% | 31.2% |
| polysorbate 20 | 0.2% | 0.2% | 0.2% |
| sodium carboxymethyl cellulose 30 mPa · s | 1% | 1% | 1% |
| benzyl alcohol parenteral | 1.5% | 1.5% | 1.5% |
| disodium hydrogen phosphate anhydrous | 0.9% | 0.9% | 0.9% |
| sodium dihydrogen phosphate monohydrate | 0.6% | 0.6% | 0.6% |
| water q.s. ad | 100% | 100% | 100% |
| pH | 7 | 7 | 7 |
| viscosity (mPa · s) | 12 | 16 | 16 |
| osmolality (mOsm)/kg | ±450 | ±450 | ±450 |
| They syringeability through a 22 G 1 ¼ needle | OK | OK | OK |

C. Pharmacological Examples

C.1. Pharmacological Testing of F1 and Analogous Oil Formulations

F1 was administered intramuscularly at 2.5 mg/kg bodyweight to four beagle dogs using a 21 G needle. In the same experiment, a similar formulation based on Miglyol™ (Fα) and one based on sesame oil (Fβ) were used, as well as a suspension comprising 9-hydroxyrisperidone decanoate in sesame oil (Fγ). The Miglyol™ formulation was also administered using a 21 G needle, but both sesame oil based formulations had to be administered using a 19 G needle. The following pharmacokinetic parameters were calculated from the experimental data:

| | $C_{max}$ (ng/ml) | $T_{max}$ (h) | $AUC_{0-672\,h}$ (ng.h/ml) | $C_{av}$ (ng/ml) | $C_{672\,h}$ (ng/ml) |
|---|---|---|---|---|---|
| F1 | 54.6 (±7.3) | 276 (±80) | 18210 (±1350) | 27.1 | 8.8 (±4.7) |
| Fα | 86.5 (±33.2) | 234 (±82) | 22082 (±6319) | 32.9 | 2.5 (≦2.0–7.8) |
| Fβ | 21.9 (±9.4) | 210 (±84) | 7054 (±3489) | 10.5 | 4.2 (≦2.0–6.5) |
| Fγ | 33.1 (±18.2) | 132 (±42) | 13875 (±6208) | 20.6 | 12.0 (±5.6) |

What is claimed is:

1. A pharmaceutical composition in the form of a depot formulation for administration by intramuscular or subcutaneous injection, comprising:

(1) as an active ingredient a therapeutically effective amount of a 9-hydroxyrisperidone fatty acid ester having the formula

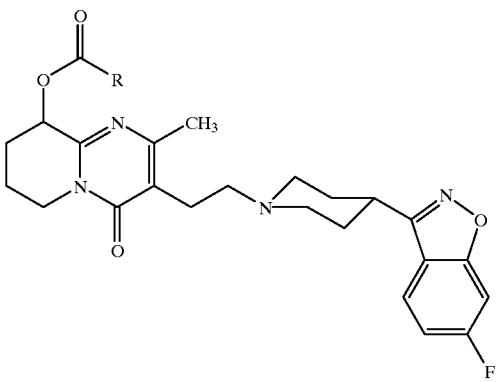

or a salt, or a stereoisomer or a stereoisomeric mixture thereof, wherein R represents a straight $C_{9-19}$alkyl radical; and (2) a pharmaceutically acceptable carrier;
characterized in that the pharmaceutically acceptable carrier is water and the active ingredient is suspended therein.

2. A composition according to claim 1 wherein R represents a straight $C_{15}$ (pentadecyl) chain and the active ingredient is 9-hydroxyrisperidone palmitate ester.

3. A composition according to claim 1 wherein the composition further comprises a suspending agent and a wetting agent, and optionally one or more of a preservative, a buffer and an isotonizing agent.

4. A composition according to claim 3 wherein the suspending agent is sodium carboxymethyl cellulose and the wetting agent is polysorbate 20.

5. A composition according to claim 4 wherein the preservative is benzyl alcohol and the isotonizing agent is mannitol or a phosphate buffer.

6. A composition according to claim 1 having a viscosity of less than 75 mPa.s.

7. A composition according to claim 1 comprising by weight based on the total volume of the composition:

(a) from 3 to 20% (w/v) of the active ingredient;

(b) from 0.05 to 0.2% (w/v) of a wetting agent;

(c) from 0.5 to 2% (w/v) of a suspending agent;

(d) up to 2% (w/v) preservatives;

(e) optionally one or more isotonizing agents sufficient to render the composition isotonic with serum; and (f) water q.s. ad 100%.

8. A process of preparing a pharmaceutical composition as claimed in claim 1 comprising intimately mixing the active ingredient with the carrier.

9. A process according to claim 8 comprising the steps of:

(a) stirring the wetting agent with the water;

(b) adding the preservative to the mixture while stirring;

(c) dispersing the suspending agent in the mixture while stirring;

(d) optionally dissolving the isotonizing agent in the mixture while stirring;

(e) dispersing the active ingredient in the mixture while stirring, followed by homogenizing the mixture.

10. A method of treating a warm-blooded animal suffering from a disorder selected from schizophrenia, non-schizophrenic psychoses, behavioral disturbances associated with neurodegenerative disorders, e.g., dementia, behavioral disturbances in mental retardation and autism, bipolar mania, depression, or anxiety, comprising administering to the warm-blooded animal a therapeutically effective amount of the composition of claim 1.

* * * * *